(12) United States Patent
Mielekamp

(10) Patent No.: US 7,225,011 B2
(45) Date of Patent: May 29, 2007

(54) HEART MODELING USING A TEMPLATE

(75) Inventor: Pieter Maria Mielekamp, Eindhoven (NL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 460 days.

(21) Appl. No.: 10/296,868

(22) PCT Filed: Mar. 28, 2002

(86) PCT No.: PCT/IB02/01042

§ 371 (c)(1),
(2), (4) Date: Nov. 26, 2002

(87) PCT Pub. No.: WO02/080108

PCT Pub. Date: Oct. 10, 2002

(65) Prior Publication Data

US 2004/0002660 A1    Jan. 1, 2004

(30) Foreign Application Priority Data

Apr. 2, 2001    (EP) .................................. 01201200

(51) Int. Cl.
*A61B 5/05*    (2006.01)
(52) U.S. Cl. ....................... 600/407; 600/416; 382/128; 382/130; 382/154; 382/156; 345/419
(58) Field of Classification Search ................. 600/413, 600/416; 382/161, 128, 131, 154
See application file for complete search history.

(56) References Cited

U.S. PATENT DOCUMENTS

| | | | |
|---|---|---|---|
| 4,945,478 A * | 7/1990 | Merickel et al. ............ 382/131 |
| 5,151,856 A | 9/1992 | Halmann | |
| 5,175,733 A * | 12/1992 | Garreau et al. ............. 382/130 |
| 5,175,773 A * | 12/1992 | Garreau et al. ............. 382/130 |
| 5,715,449 A * | 2/1998 | Peters et al. ................ 707/102 |
| 5,734,739 A | 3/1998 | Sheehan | |
| 5,768,405 A * | 6/1998 | Makram-Ebeid ............ 382/128 |
| 5,872,861 A * | 2/1999 | Makram-Ebeid ............ 382/130 |
| 5,889,524 A * | 3/1999 | Sheehan et al. ............ 345/419 |
| 6,047,080 A * | 4/2000 | Chen et al. ................. 382/128 |
| 6,047,090 A * | 4/2000 | Makram-Ebeid ............ 382/257 |
| 6,073,042 A * | 6/2000 | Simonetti ................... 600/420 |
| 6,169,917 B1 * | 1/2001 | Masotti et al. ............. 600/407 |

FOREIGN PATENT DOCUMENTS

| | | |
|---|---|---|
| EP | 0 383 697 | 9/1990 |
| WO | WO 99/55233 | 11/1999 |
| WO | WO 00/10034 | 2/2000 |

OTHER PUBLICATIONS

Smets et al.; 1990; International journal of Cardiac Imaging; vol. 5; pp. 145-154.*

* cited by examiner

*Primary Examiner*—Brian L. Casler
*Assistant Examiner*—James Kish

(57) ABSTRACT

A device, a method and a computer program to model and report an anatomic structure, for example for coronary angiography is provided. The graphical editor models and reports the morphology/topology of the coronary anatomy with its clinical relevant items, i.e. grafts, stents, stenosis/occlusion and turtuosity. From the model different presentations (views) with adjustable display attribute settings, like scale and shape of the arteries can be constructed.

8 Claims, 5 Drawing Sheets

HEART MODELING USING A TEMPLATE

The invention relates to a device for describing and evaluating a three-dimensional anatomical structure.

The invention further relates to a method for describing a three-dimensional anatomical structure.

The invention still further relates to a computer program for describing and evaluating a three-dimensional anatomical structure.

Devices are known which can calculate and output graphically a simulation of functional processes of anatomical structures, for example the flow of blood through an arterial system. If the simulation is to be matched to characteristics of an individual, for example if the aim is to examine constrictions or other abnormalities in the blood vessels with regard to their effects on the blood flow, it is required to input these abnormalities manually, for example by specifying the site of the abnormality and of a constriction of the flow cross section at this point.

However, such a device can be supplemented only within the framework of the prescribed model, and this signifies a limitation, particularly due to the fact that the anatomical structures vary strongly individually. Moreover, in many cases it is not necessary to obtain a simulation of the function of the anatomical structure, for example of an organ, it is merely desirable, rather, to obtain a storable and unambiguous evaluation of examination results that is as simple as possible.

It is an object of the invention to provide a device as described in the opening paragraph, wherein a reporting of the examination results is enabled in a simple way.

The device according to the invention comprises an input means to input said structure, an output means, to output a simplified two-dimensional image of said structure based on a pre-stored image template, said device being arranged to graphically supplement said image with individualized details, the device being further arranged to carry out an automated assignment of the details to the anatomical structure.

According to the technical measure of the invention the user can start from templates describing standard morphologies. These morphologies can be modified graphically byte user by means of the input means, such as a keyboard, a touch screen, a mouse or any other suitable input means. Such a modification can enable moving operations, adding deleting, cut/paste and transformation operations on the structures of the template. The template can comprise a graphical model of the clinically relevant structures. The structures can be annotated with relevant clinical information. For instance, coronary artery lesions can be described by their location, severity and classification. Additional information can be enabled, such as, by way of non-limiting example, a color coding of the severity of the stenosis. Due to the fact that in accordance with the invention the device supplies a simplified two-dimensional representation, this basic representation need not be prepared by the examining physician, something which signifies an easing of work. Further details which have been obtained, for example, via x-ray examinations or other imaging methods for a respective individual can then be supplemented on the basic structure output by the device. Due to the fact that the device carries out a classification of supplemented details relating to the anatomical structure in an automated fashion, the device takes over work which would otherwise have to be undertaken by the operator, for example a physician.

In an embodiment, the device according to the invention comprises evaluation means arranged to evaluate shape, size, nomenclature and/or type of the details in an automated fashion, said device further comprising means arranged to produce a text report comprising evaluation results. The template of a structure, for example of an artery tree can be stored electronically, printed-out, modified and published through a network. The text report can be stored in a database and can be made available via the database for further reporting. By means of incorporation of a document component technology, like activeX, the artery documents can be included as objects and in-place activated in container programs like document editors (Word or the like) and different Internet browsers (Explorer). The information content of the output text report is not limited to the graphic presentation, but it is possible for purposes of a statistical analysis, for example to make use of a text report which is of the same format in each case and therefore comparable between the patients. This transmission of the graphic representation in the text report can be undertaken without action by the user, and therefore without creating a workload. Additionally, it is advantageous to insert the tool in a more general workflow context, the artery information can be related to the Radiology Information System (RIS) information in this way it will be possible to create multi-media documents, where the model information and text report arc linked to real image data and can be simultaneously updated. An example of such a link is a hyperlink. According to this technical measure an automatic reporting is enabled. In order to support automatic report generation the document model must be supplied with a structure and nomenclature of The anatomic structure. This can be done by means of a hierarchical data structure, which will be explained in more detail with reference to figures.

A still further embodiment of the device according to the invention is characterized in that the device is arranged to undertake an automated amendment of an alpha-numerical information to the details or their parts. The automated assignment of supplemented details can consist with particular advantage of naming comprising an alpha-numerical information. For example, if the name of an artery is known, and the artery is divided into segments each segment can be named with the associated technical term using nomenclature available to the device. The data of the segment thus named can further be taken over into a text report in an automated fashion. The naming of the main artery can likewise be performed in an automated fashion, in which case, for example, the device puts forward a proposal for a name of the respective anatomical structure, for instance the main artery, with the aid of the marked geometry. This name can then be verified by the user, for example a physician, or changed as required. The names of the arteries are, thus, partly static partly dynamic parameters. The names of the main arteries, like Left Anterior Descending (LAD), Right Coronal Ascending (RCA) and Circumflex arc determined by the physiology and are prescribed automatically. The association of these names with the model of the simplified image can be made at forehand in the template. For naming of sub-segments a more detailed model is required. For instance, the boundaries between the proximal, mid and distal artery segments of the LAD are determined by the locations of the first and the third diagonal branch segments. The branches are ordered along their parent curves by means of the branch-index and this provides a solution for the dynamic naming of the artery segments.

A still further embodiment of the device according to the invention is characterized in that the device is arranged to undertake an automated assignment of the details to a front or a back surface of the anatomical structure. According to this technical measure the simplified two-dimensional image of the anatomical structure can be evaluated internally as a three-dimensional structure. For example, when inscribing a detail, such as an artery, which crosses an edge contour of the image, the artery is automatically judged as a connection between the front and the back of the structure and its course is appropriately indicated and stored.

A still further embodiment of the device according to the invention is characterized in that the device is arranged to undertake an automated calculation of a functionality of the anatomical structure with reference to abnormal regions. It is likewise particularly favorable in the case of marked abnormalities, for example in the case of occlusions, for the device to be able to represent in an automated fashion the blood flow downstream of the disorder as being reduced or stopped.

It must be noted that the device according to the invention is preferably arranged to allow an image manipulation by the user, for example a deformation of the structure and/or a displacement of structure elements relative to each other. The displacement of the arteries can optionally be undertaken particularly favorably with a constant inosculation angle over a curve, or with a constant position of the sub-artery, in which case the inosculation angle could then be changed in an automated fashion and calculated in each case by the device.

Further advantages and details of the invention follow from exemplary embodiments of the subject matter of the invention which are described below and illustrated in the drawings.

Figure 1:
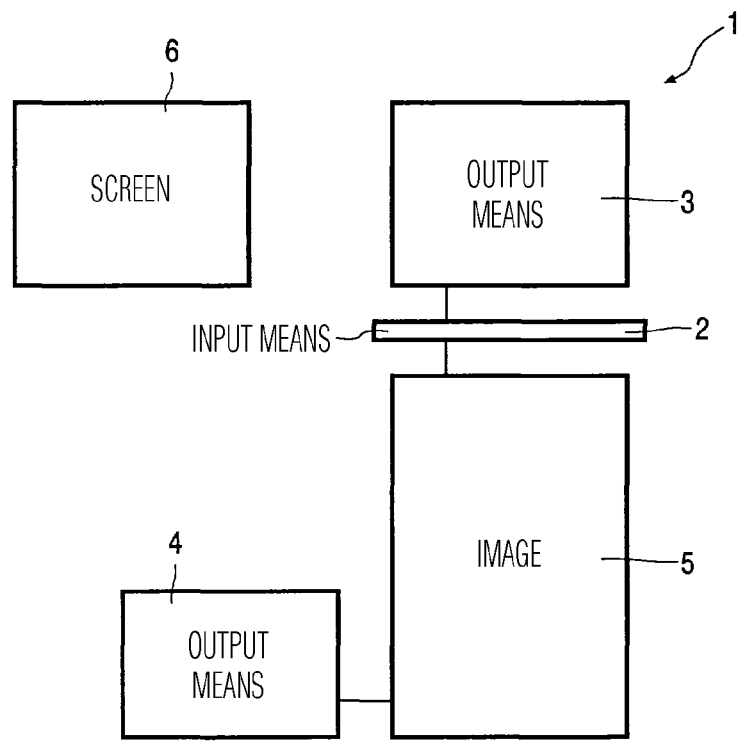
FIG. 1 shows a schematic view of the parts of the device according to an embodiment of the invention.

FIG. 1 shows a schematic view of the parts of the device according to an embodiment of the invention. The device 1 illustrated by way of example comprises a keyboard as input means 2 and a display screen as output means 3. A further output means 4, for example a printer or a plotter or a connection to a local or global network, for example the Internet, can be included. A simplified two-dimensional image 5 of an anatomic structure, for example a human heart, is output on the display screen 3 and/or on a further output means 4 of the device 1. By using, for example, a series of diagnostic examination data obtained, for example in an angiographic examination, a series of X-ray images can be presented on a screen 6. The user of the device 1 can then make a selection between a plurality of the simplified images 5 also referred to as templates, which are stored in the device 1. These simplified images 5 are selected on the basis of their correspondence to the basic shapes as observed on the screen 6. For example, there is a fundamental distinction between a left-dominant and a right-dominant type. Alternatively, it is also possible for the selection to be undertaken by the device 1 in an automated fashion via an image recognition, for example, via evaluation of X-ray images. With the aid of the examination data, which are generally formed by multiple images from different views, details can then be added to the simplified image as graphic elements either via automatic image recognition or in dialogue with the user, in order to supplement the two-dimensional basic structure 5 with relevant details. The image supplemented in such a way can be available overall as a file, for example, and can be inserted as such, for example, as an activeX element, in comprehensive programs, for example, in text processing programs or in an Internet browser. Again, the file can be embedded as a whole in a workflow context, in order thereby, for example, to permit multimedia outputs in which the model output of the heart can be compared with the actual heart images, or in which, for example, in addition to the model representation a text file is also created with the relevant data from the graphic conditioning.

Figure 2:
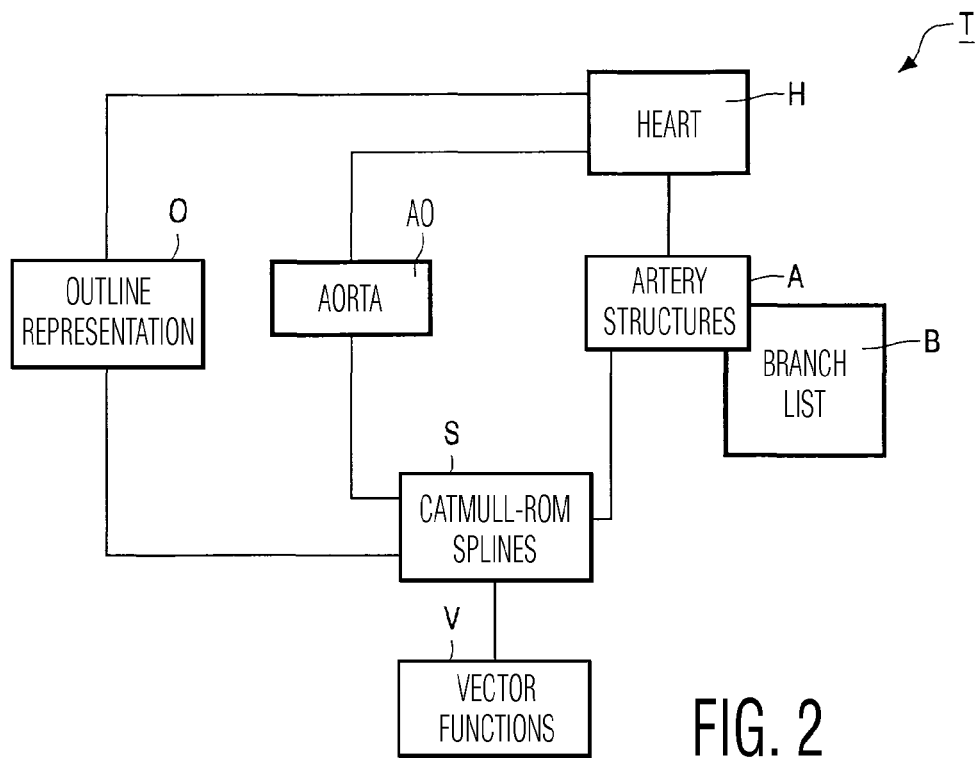
FIG. 2 shows an embodiment of a hierarchical data structure utilized by a template according to the invention.

FIG. 2 shows an embodiment of a hierarchical data structure utilized by a template according to the invention. In order to create a simplified two-dimensional image of the anatomical structure being reported, the device is supplied with a template T. The template T campuses a structure and nomenclature in a generalized way of the anatomical structure. The embodiment of the template is discussed by way of example for a coronary artery tree. The heart and the coronary artery can be modeled by means of the hierarchical data structure given by the template T. The logical build-up of the template is like a tree, or a groove which can contain more than one tree. At the lop level a list of artery structures (A) is maintained. The origins of the structures are constrained to the aorta (AO). Each artery structure (A) contains a branch list (B), which is pre-filled according to medical knowledge. The branch list can also contain an index which serves to position a certain branch within its parent artery. All arteries are connected, and each artery belongs to a parent artery, which is at the top level of the aorta. The arteries are graphically modeled by means of Catmull-Rom splines (S), comprising vector functions (V), which are explained in more detail with reference to FIG. 4. The aorta itself can be modeled as an artery of the highest level, or can be modeled as apart of the heart by means of a description of two-dimensional contours. The final outline representation (O) of the simplified two-dimensional image is modeled and displayed by a recursive display routine. By using a suitable algorithms the z-ordering of the arteries can be realized and is based on their relative positions in the branch list (B). Therefore, the overlapping arteries will be visualized accordingly on a front or a back surface of the heart. It is clear that removing an artery sub-tree simply involves a removing of the corresponding branch from its parent branch-list. A selected artery sub-tree can be moved relative to its parent artery by a modification of its branch index. It is possible by means of a suitable indexing to move a branch within an artery or to connect a branch to a different artery. Pasting or copying of a sub-tree to a destination artery is done by attaching the sub-tree to a destination artery of a given index, which is calculated from the indicated destination position. The destination position can be made known to the device by the input means.

Figure 3:
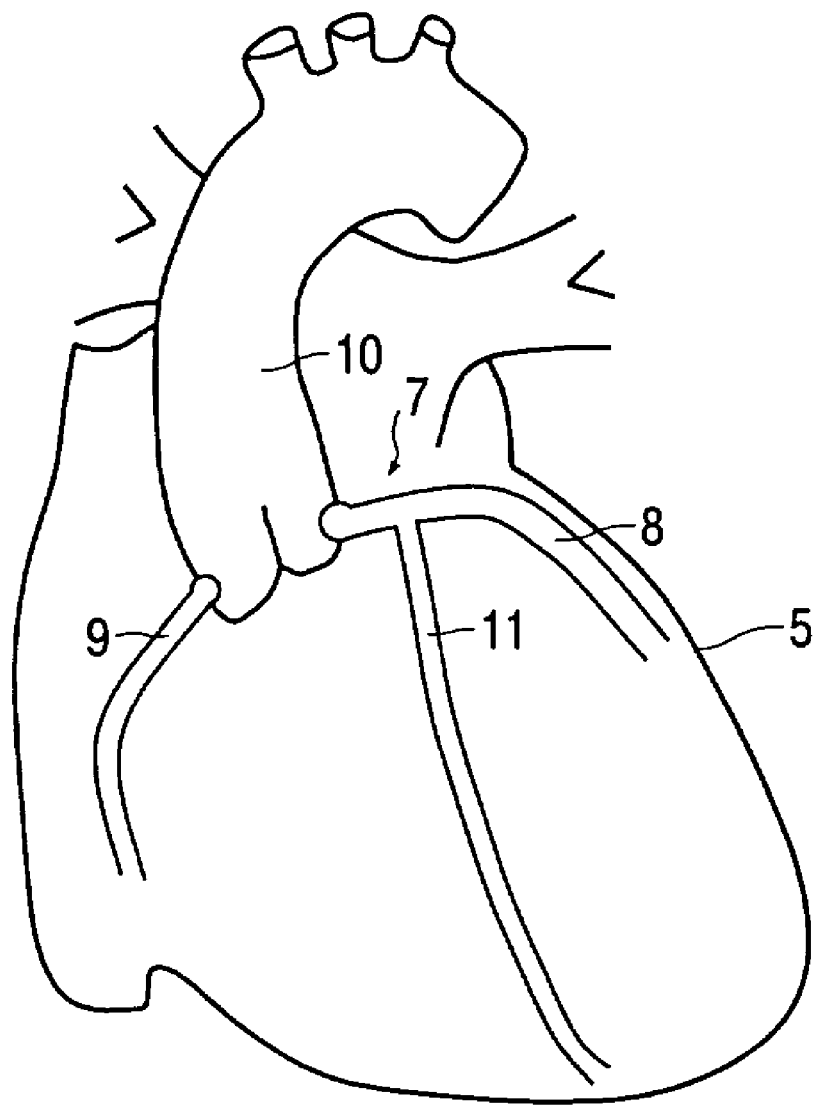
FIG. 3 shows an illustration of a standardized classification and nomenclature of the system of coronary arteries, the segments of which are named in accordance with a template.

FIG. 3 shows an illustration of a standardized classification and nomenclature of a system of coronary arteries, the segments of which are named in accordance with a template. In the FIG., two arteries 8 and 9 which branch off from the aorta bow 10 are illustrated by way of example. A sub-artery 11 branches off in this case from the artery 8. The marked blood vessels 8, 9 therefore form a first hierarchy level, the sub-artery 11 being subordinate thereto. In order to illustrate the arteries the device according to the invention comprises a template where corresponding midlines of the arteries are simulated by means of, for example Catmull-Rom splines, which are explained in more detail with reference to FIG. 4. An initial width exhibited by the arteries about these spline functions is likewise prescribed by the device, the width varying depending on the hierarchy level: a main artery is allocated a greater width than a sub-artery. A second sub-level, branching off therefrom in turn, is output with an even narrower cross section. The cross-sectional width of the arteries output by the device, or of other anatomical structures can, in addition, vary automatically over the longitudinal course of the spline function, for example in such a way that the width of the artery decreases with increasing length thereof. It goes without saying that the width of the artery and the course thereof can also be matched in each case to individual findings.

Figure 4:
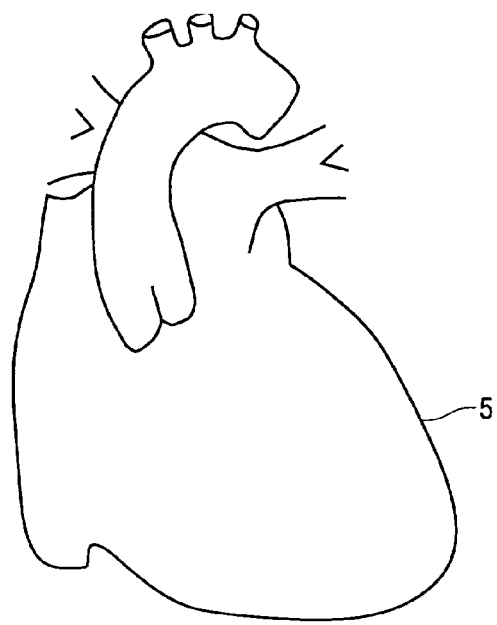
FIG. 4 shows an illustration of a possible two-dimensional projection that can be output by the device as a simplified two-dimensional image.
Figure 4A:
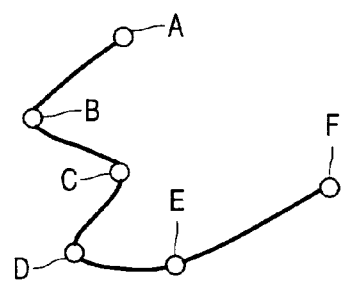
FIG. 4a shows a schematic of a Catmull-Rom spline function defined by six control points.

FIG. 4 shows an illustration of a possible two-dimensional projection that can be output by the device as a simplified two-dimensional image 5. For cardiac application it is a simplified basic image of a heart contour. The relevant clinical information can be added to this simplified image by means of Catmull-Rom splines. The course of the representation of a Catmull-Rom spline function is illustrated in FIG. 4a. Six control points A, B, C, D, E, F, which can be displaced, are marked. An individual segment of the function graph, for example a section extending between the points B and C, is defined by four consecutive control points, in this case the control points A to D. For edge regions of the function graph, the outer control point, that is to say A or F, is repeated in place of the fourth control point for the definition of the spline function. Consequently, by way of example the shape of the segment E–F is a function of the control points D to F.

New arteries can be formed by using new spline control points, something which is possible, for example, via an input aid such as a mouse, a joystick or other drawing aids. Control points can be displaced, inserted and extinguished in order to vary the shape of an artery. It is possible in this case, for example, to click on the artery, which is illustrated by the spline function, in the near zone of one of its control points A, B, C, D, E, F, for example via a mouse, and to drag this near zone to a new site with the aid of the mouse. The control point is then displaced to the new site, the spline function on which the artery is based being correspondingly displaced. This displacement is terminated upon release of a depressed mouse key, for example.

Figure 4B:
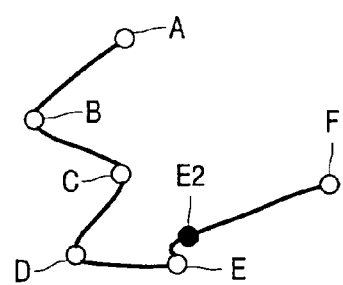
FIG. 4b shows a similar view to FIG. 4a in relation to an insertion of a new control point.
Figure 4C:
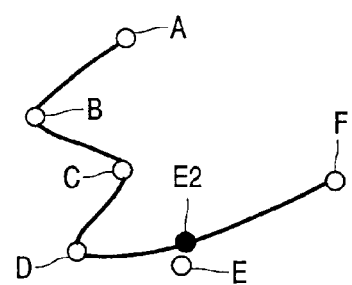
FIG. 4c shows a similar view to FIG. 4b after extinction of a control point.

If, by contrast, the artery is clicked on in an interspace between control points, a new control point is created (compare FIG. 4b, in which the control point E2 has been newly created). The old control point E is then automatically extinguished upon release of the mouse key or the like, the result being the new configuration of the curve corresponding to FIG. 4c through the new control point E2.

It is not necessary in the case of this method for individual control points to be calculated or displaced, rather it is sufficient for the artery to be touched at any site by the drawing aid in order to match the spline function appropriately. The user therefore need not have any sort of knowledge of mathematical background.

Figure 5:
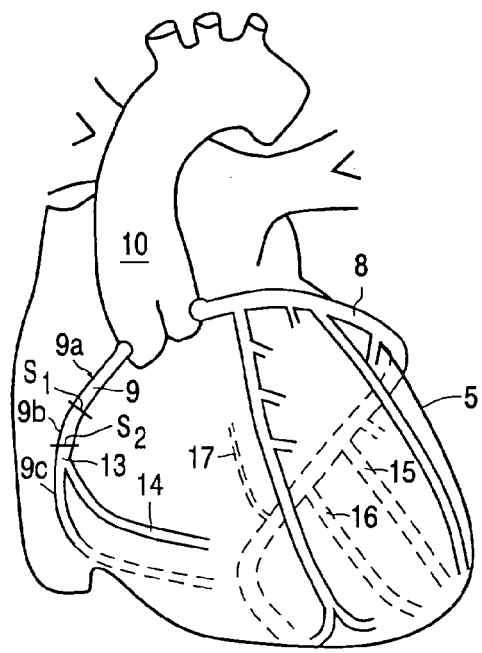
FIG. 5 shows an illustration of an embodiment of an elaborate representation of an arterial tree.

A more elaborate presentation of an embodiment of a cardio-vascular tree is schematically given in FIG. 5. The arteries 8 and 9 have been added to the template of FIG. 4. The device 1 is arranged to automatically assign the arteries 8 and 9 of the three-dimensional structure, which is illustrated only as a two-dimensional picture in FIG. 5, and to detect, for example which parts of said arteries 8, 9 are to be assigned to the front of the heart and which to the back of the heart. This assignment can be illustrated graphically on the monitor screen by lighter walls as contrasted with darker walls and can be performed without any action of a user. This assignment is possible in an automated fashion because the device 1 stores data according to their three-dimensional order. It is also possible, for example, to undertake a rotation of the anatomic structure in order thereby to view this structure from different directions.

It follows therefrom that, for example, even in the case of the sub-artery 14 that is marked in FIG. 5 and inosculates with the artery 9 at the point 13, it is also possible for the device 1 to detect that this inosculation 13 lies on the front of the heart. The illustration is undertaken by the device correspondingly. By contrast therewith, the sub-arteries 15, 16 and 17 marked in FIG. 5 lie on the back of the heart, and this is automatically assigned by the device 1 likewise in the case of marking these sub-arteries.

In addition, the artery 9 has been split up in FIG. 5 into the individual segments 9a, 9b and 9c by inserted segment boundaries S1 and S2. Given known names of the artery 9, the device 1 automatically names these individual segments in accordance with the nomenclature standard specified in FIG. 1, which is taken from the ACC/AHA Guidelines for Coronary Geography, Journal of the American College of Cardiology, Vol. 33, No. 6, 1999. The position of the marked segment boundaries is included. The assignment of the branching 13 to the segment 9c is marked, so that it is then possible to output automatically in the patient report the point at which a sub-artery 14 inosculates with the main artery 9. The junction 13 can then be displaced by the user, it being possible upon crossing of the segment boundary S2 or later S1 for the device 1 to rename automatically the position of the junction 13, without any action of the user. The text report would therefore automatically be adapted by the device 1, which recognizes the position of the sub-artery 14 relative to the main artery 9.

As is explained earlier the arteries are created by the indication of the control-points. All top-level arteries are constrained to the aorta. Their origin is forced to be within the boundary region of the aorta. Artery branches are created with reference to their parents, by indication of the connection point. This attachment position is converted to the branch-index along the destination spline. The discrimination of the arteries, as being connected to the aorta or as branches to other arteries is made on the basis of the position of the first point.

In order to interact with an individual artery, the target spline must be selected, in which case it is highlighted. A specific spline can be selected by the user by input means. The selection can be made undone by selecting another spline or by any other appropriate way. By changing the relative position of the control points along the selected spline the coarse of the corresponding artery can be modified.

Figure 5A:
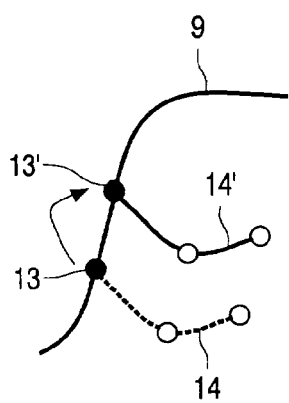
FIG. 5a shows an embodiment in which a branch of a sub-artery is moved.

It is also possible to change the position of the branches on the artery. To move a branch relative to a parent its index must be modified to a new position. By changing the index of the branch the branch can be moved along the parent artery. As follows from FIG. 5a, the sub-artery 14 can be displaced relative to the main artery 9 by using the drawing aid to access the point of intersection 13 or its near zone and to displace it along the main artery. It is not necessary in this case to hit the point of intersection 13 exactly, instead it suffices for the near zone of the branching-off point 13 to be clicked on or the like. The position of the new point of intersection, which is formed at the new branching-off point 13', is calculated in such a way that said point lies in each case on the main artery 9. This automatically ensures that the branching-off point of the sub-artery 14' lies on the main artery 9 and cannot be offset next to said main artery, something which would be anatomically incorrect. A compulsory adaptation to the anatomical conditions is thereby automatically ensured by the device 1 and the computer program stored therein in the exemplary embodiment.

Figure 5B:
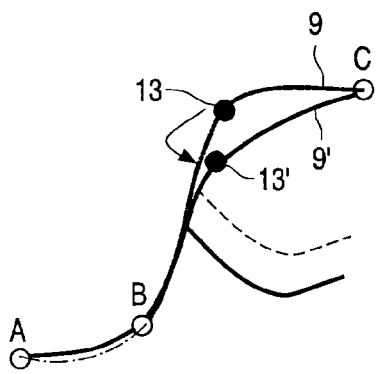
FIG. 5b shows an embodiment of a displacement of the main artery.

Instead of the displacement of sub-arteries, for example, the sub-artery 14, it is also possible to vary the main artery, for example artery 9, the branching-off point 13 for the sub-artery 14 also being moved in this case such that, as may be seen from the mathematical model in FIG. 5b, the ratio of the distances of the branching-off point 13 from the control point B, compared with the distance of the branching-off point 13 from the control point C, automatically remains constant. Consequently, the change in the main artery due to a displacement, of the control point B here, by way of example, is automatically attended by a displacement of the branching-off point 13. Due to the automatic adaptation of the shape and length ratios in the case of this variation, the device also automatically changes all the names of the anatomical structures, for example of the arteries and sub-arteries, up to possibly newly set segment boundaries, thus rendering possible any desired change in shape by the user without the latter having to think about adapting the naming.

This has the following significance for a displacement of segment boundaries S1, S2 shown in FIG. 5 when applied to the representation of arteries: in the case of a displacement of the segment boundaries S1, S2 undertaken by the user, the length ratios of, for example, a branching-off point 13 in the segment 9c remain constant relative to the boundaries thereof, that is to say in the case, for example, of a displacement of the segment boundary S2 in the direction of S1, the device 1 would automatically also displace the branching-off point 13 of the sub-artery 14, such that the distance thereof from the segment boundary S2 in relation to the total length of the section 9c would be kept constant.

Figure 5C:
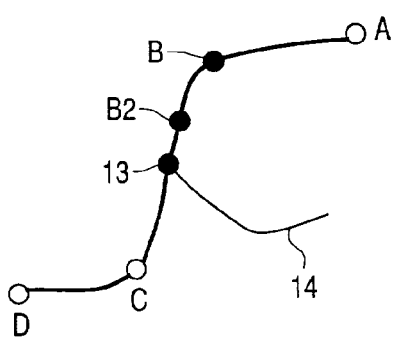
FIG. 5c shows an insertion of a new control point above the simulated branching-off point of a sub-artery.
Figure 5D:
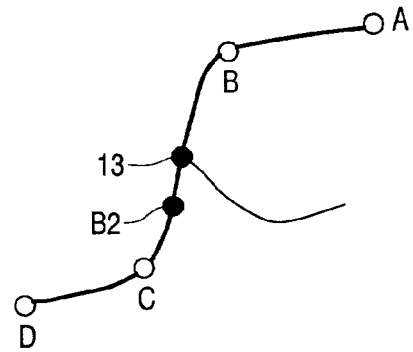

FIGS. 5c and 5d illustrate the insertion of new control points by clicking on the function graph, which stands schematically for an artery, outside the near zone of a control point. This results in different consequences depending on the site at which a new control point, denoted here as B2, is inserted. The new control point B2 is inserted in FIG. 5c between the previous control points B and C, specifically in such a way that it is positioned between the control point B and a branching-off point 13 for a sub-artery 14. The position of the branching-off point 13 is thereby automatically moved to the section between the control points B2 and C. A displacement of the point B, for example, would be insignificant for the position of the branching-off point 13 below. If, by contrast, the control point C were displaced, then according to the illustration in FIG. 5b the connecting point 13 would also be moved in such a way that the ratio of the distances between the point C and junction 13, on the one hand, and the point B and connecting point 13, remains constant. The conditions are reversed in FIG. 5d, since there the new control point B2 has been inserted between the branching-off point 13 and the control point C. Correspondingly, a movement of the point C would leave the branching-off point 13 constant, whereas a displacement of the point B would entail a co-movement of the branching-off point 13 for the purpose of keeping the relative distances constant. Additionally, it is also possible to perform a displacement of sub-arteries in parallel to itself, or alternatively by preserving an inosculation angle with respect to the parent artery.

It can be clear from all of the above that removing an artery sub-tree simply involves removing the corresponding branch from its parent list. As described before a selected artery sub-tree can be moved relative to its parent artery by a modification of its branch index. Pasting/copying of a sub-tree to a destination artery can be done by attaching the sub-tree to a destination artery at a given index, which can be calculated from the indicated destination position.

Figure 6:
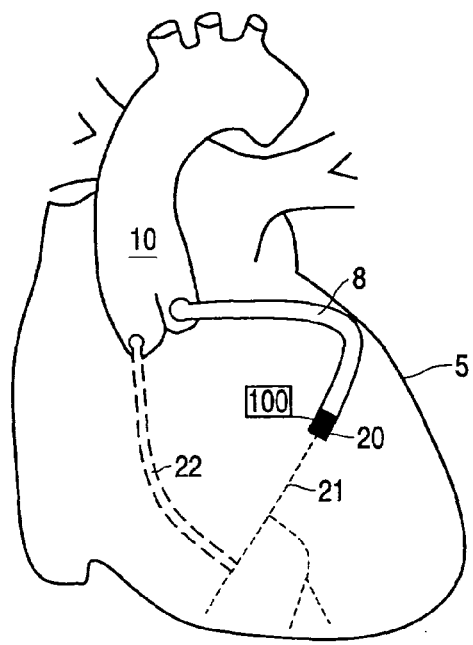

FIG. 6 presents in a schematic way an embodiment of annotations added to an image of the anatomical structure being examined. It is likewise possible to use a menu to select from a group of abnormalities, for example occlusions (lesions), calcifications, thrombus, ectasia, dissections. It is possible to arrange the hierarchical data structure in such a way that every artery contains an annotation list. Each annotation has a start and an end index position. By using these index positions the annotated elements are tagged to the geometry of the arteries. If a spatial position of an artery is modified by user interaction the corresponding annotation is moved accordingly due to its index, being referred to the index of the artery For example, a blood flow 21 can be shown in each case downstream of an abnormality, for example the occlusion 20 marked in FIG. 6, the length of which can be marked in the illustration and is evaluated by the device 1. It is possible in this process to calculate a complete arterial occlusion or a partial arterial occlusion, and to output it via the output means. The blood flow is shown variously, as appropriate. The vessel 21 no longer supplied with blood is illustrated in FIG. 6 as a dashed line. A restoration of a vessel section no longer supplied with blood per se can also be represented in an automated fashion by the device 1 via grafts or similar auxiliary lines from another main artery. For example, to restore the supply of the regions 21 otherwise no longer supplied with blood an additional vessel 22 can be introduced. The region 21 then acquires a representation which makes clear, on the one hand, that it is no longer being regularly supplied and that, on the other hand, supply has been restored via a bypass line 22. It is thereby possible, for example, for the measure that is to be taken in an operation to be simulated in advance. It is also possible to show the region 21 lying at the back surface of the heart. Additionally, collaterals can be marked, which can be performed in an automatic way. Each of the marked abnormalities is recorded with regard to its dimensions and severity (percentage value) and can also be represented with the aid of these data with more precise localization from the graphics in the text report.

Figure 7:
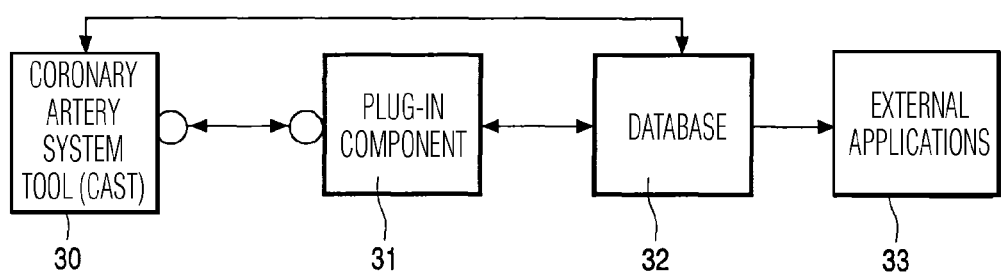

As is illustrated in FIG. 7, the data produced in the visualization, denoted there as CAST (Coronary Artery System Tool) 30, can be stored in a database, denoted there as Cardiology Information System Data Base. The data stored there are also available for external applications such as, for example, document editors, mail tools, browsers for the Internet etc. The information is available not only as graphic data, but also, via its storage in the database, as text files for statistical analyses and the like, there being no need for any graphical evaluations for applications of this sort. The data obtained can therefore be exchanged between completely different systems, for example, beyond frontiers, without it being necessary to accommodate a possible plurality of medical or scientific processing teams. For this purpose, the anatomical structures are stored in the database as network models and are assigned clearly via their position, dimensions and their nomenclature.

The arterial length is calculated in each case along the spline functions, and a respective point thereon is stored as a percentage of the total length from the start of an artery at the aorta up to its point (apex) lying remote therefrom. Likewise, the lengths of the arterial segments and any abnormal elements are marked and stored in the same way by their relative position. The position of sub-arteries and diseased features is stored via their respective relative position, with reference to the length of the higher-level structure, for example the artery, in the direction of the blood flow. The origin of a sub-artery or the midpoint of a pathological disorder is used for this purpose.

Communication between the database 32, in which it is also possible, for example, to store data for stents or other aids in a clinically specific fashion takes place in such a way that the graphics part 30 (Coronary Artery System Tool) is available as a plug-in component of the respective database 32. The plug-in component 31 can be arranged to make customised annotations of data, which are not obligatory for the graphics part. The graphics part 30 is arranged to make an association to a respective parameter in the database 32. Therefore, the changes made in the graphics part 30 are automatically updated in the database 32 and can be reported correctly, for example by means of a text report. This automatically creates an interface for incorporating the data into the system of the respective hospital 32. The actual device need not be changed for this purpose. The graphics data can be created, for example, by CAST as a Bynary Large Object (Blob) or in the XML format, and be incorporated in these formats into the respective individual patient database and can be made available for external applications 33.

The invention claimed is:

1. A device for describing and evaluating a three-dimensional anatomical structure, the device comprising:
   an input means for inputting examination data of said anatomical structure;
   an output means for outputting a simplified two-dimensional image representation of said anatomical structure, wherein the simplified two-dimensional image representation is based on a pre-stored image template the pre-stored image template including a graphical model of clinically relevant structures of the anatomical structure and a corresponding nomenclature, the template further utilizing a hierarchical data structure for modeling the clinically relevant structures;
   means for graphically supplementing said simplified two-dimensional image representation with individualized details, wherein graphically supplementing with the individualized details includes annotating with relevant clinical information, including nomenclature of the anatomical structure; and
   means for carrying out an automated assignment of the graphically supplemented individualized details to the simplified two-dimensional image representation and with respect to the examination data of the anatomical structure.

2. The device as claimed in claim 1, wherein said device comprises evaluation means arranged to evaluate shape, size, nomenclature and/or type of the details in an automated fashion, said device further comprising means arranged to produce a text report comprising evaluation results.

3. The device as claimed in claim 1, wherein the device is arranged to undertake an automated amendment of an alpha-numerical information to the details or their parts.

4. The device as claimed in claim 1, wherein the device is arranged to undertake an automated assignment of the details to a front or a back surface of the anatomical structure.

5. The device as claimed in claim 1, wherein the device is arranged to undertake an automated calculation of a functionality of the anatomical structure with reference to abnormal regions.

6. The device as claimed in claim 1, wherein the anatomical structure comprises a heart and the details comprise a cardiovascular system comprising arteries.

7. The device as claimed in claim 6, arranged to divide images of the arteries into individual segments, said device being further arranged to undertake an automated naming of the segments of the arteries.

8. A method for describing a three-dimensional anatomical structure, comprising:
   performing an inputting of individual examination data of the anatomical structure into a device for processing the data;
   performing an outputting of a simplified two-dimensional image representation of the anatomical structure, wherein the simplified two-dimensional image representation is based on the individual examination data and a template, the template including a graphical model of clinically relevant structures of the anatomical structure and a corresponding nomenclature, the template further utilizing a hierarchical data structure for modeling the clinically relevant structures;
   supplementing the simplified two-dimensional image representation with individualized graphic details, wherein supplementing with the individualized graphic details includes annotating with relevant clinical information, including nomenclature of the anatomical structure; and
   carrying out an automated assignment of the individualized graphic details relative to said simplified two-dimensional image representation and with respect to the examination data of the anatomical structure.

* * * * *